United States Patent
Shriner et al.

(10) Patent No.: US 11,864,915 B2
(45) Date of Patent: Jan. 9, 2024

(54) EAR-WORN ELECTRONIC SYSTEM EMPLOYING WIRELESS POWERING ARRANGEMENT FOR POWERING AN IN-EAR COMPONENT DURING SLEEP

(71) Applicant: Starkey Laboratories, Inc., Eden Prairie, MN (US)

(72) Inventors: Paul Anders Shriner, Minneapolis, MN (US); Ezdeen Elghannai, Eden Prairie, MN (US); Stephen Paul Flood, Eden Prairie, MN (US); Gregory J. Haubrich, Champlin, MN (US); Zhenchao Yang, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 474 days.

(21) Appl. No.: 17/206,347

(22) Filed: Mar. 19, 2021

(65) Prior Publication Data
US 2021/0298676 A1 Sep. 30, 2021

Related U.S. Application Data

(60) Provisional application No. 63/000,179, filed on Mar. 26, 2020.

(51) Int. Cl.
*A61B 5/00* (2006.01)
*A61M 16/06* (2006.01)

(52) U.S. Cl.
CPC .......... *A61B 5/6817* (2013.01); *A61B 5/7475* (2013.01); *A61M 16/06* (2013.01);
(Continued)

(58) Field of Classification Search
CPC .............................................. A61B 2560/0214
(Continued)

(56) References Cited

U.S. PATENT DOCUMENTS 5,606,621 A 2/1997 Reiter et al.
6,253,871 B1 7/2001 Aceti
(Continued)

OTHER PUBLICATIONS

File History for U.S. Appl. No. 15/654,193, filed Mar. 18, 2021, 252 pages.

*Primary Examiner* — Jerry D Robbins
(74) *Attorney, Agent, or Firm* — Mueting Raasch Group

(57) ABSTRACT

An ear-worn electronic monitoring system includes an on-ear component comprising a housing configured for placement on, in or about the wearer's ear. The on-ear component comprises a power source and a first interface coupled to the power source. The monitoring system also includes an in-ear component comprising a housing configured for deployment at least partially within an ear canal of the wearer. The in-ear component comprises a second interface configured to couple to and decouple from the first interface, a controller coupled to a memory, one or more physiologic sensors coupled to the controller and memory, and power management circuitry coupled to the controller. The power management circuitry comprises a wireless power receiver configured to receive power from a wireless powering arrangement. The power management circuitry is further configured to receive power from the power source of the on-ear component when the second interface is coupled to the first interface.

27 Claims, 6 Drawing Sheets

(52) U.S. Cl.
CPC .............. *A61B 2560/0214* (2013.01); *A61B 2560/0271* (2013.01); *A61B 2560/0475* (2013.01); *A61B 2562/227* (2013.01)

(58) Field of Classification Search
USPC ........................................................ 320/108
See application file for complete search history.

(56) References Cited

U.S. PATENT DOCUMENTS

| | | |
|---|---|---|
| 6,320,969 B1 | 11/2001 | Killion |
| 6,510,230 B2 | 1/2003 | Marx |
| 6,643,378 B2 | 11/2003 | Schumaier |
| 6,821,249 B2 | 11/2004 | Casscells, III et al. |
| 8,116,494 B2 | 2/2012 | Rass |
| 8,625,830 B2 | 1/2014 | Probst et al. |
| 8,798,294 B2 | 8/2014 | Havenith et al. |
| 8,842,863 B2 | 9/2014 | Nielsen et al. |
| 8,867,765 B2 | 10/2014 | Solum |
| 8,978,885 B2 | 3/2015 | Gabathuler |
| 9,426,587 B2 | 8/2016 | Stoffels et al. |
| 9,451,367 B2 | 9/2016 | Basseas et al. |
| 9,968,781 B2 | 5/2018 | Roehrlein et al. |
| 10,932,068 B2 | 2/2021 | Meskens et al. |
| 2007/0274553 A1* | 11/2007 | Rass .................. H04R 25/554 381/328 |
| 2008/0146890 A1* | 6/2008 | LeBoeuf ................ A61B 7/003 600/300 |
| 2011/0286616 A1* | 11/2011 | Beck ..................... H04R 25/65 381/315 |
| 2017/0238812 A1 | 8/2017 | Atlas |
| 2018/0027343 A1 | 1/2018 | Dobson et al. |

\* cited by examiner

EAR-WORN ELECTRONIC SYSTEM EMPLOYING WIRELESS POWERING ARRANGEMENT FOR POWERING AN IN-EAR COMPONENT DURING SLEEP

RELATED APPLICATIONS

This application claims the benefit of U.S. Provisional Application No. 63/000,179, filed Mar. 26, 2020, the entire content of each of which is hereby incorporated by reference.

TECHNICAL FIELD

This application relates generally to ear-level electronic systems and devices, including physiologic monitoring devices, position/motion sensing devices, hearing aids, personal amplification devices, and hearables.

SUMMARY

Embodiments are directed to an ear-worn electronic monitoring system configured to be worn by a wearer and powered wirelessly at least during wearer sleep. The ear-worn electronic monitoring system includes an on-ear component comprising a housing configured for placement on, in or about the wearer's ear. The on-ear component comprises a power source and a first interface coupled to the power source. The monitoring system also includes an in-ear component comprising a housing configured for deployment at least partially within an ear canal of the wearer. The in-ear component comprises a second interface configured to couple to and decouple from the first interface, a controller coupled to a memory, one or more physiologic sensors coupled to the controller and memory, and power management circuitry coupled to the controller. The power management circuitry comprises a wireless power receiver configured to receive power from a wireless powering arrangement. The power management circuitry is further configured to receive power from the power source of the on-ear component when the second interface is coupled to the first interface.

Embodiments are directed to a system comprising a wireless powering arrangement which includes a power transmitter. The system also comprises an ear-worn electronic monitoring system configured to be worn by a wearer and powered wirelessly at least during wearer sleep by the wireless powering arrangement. The ear-worn electronic monitoring system includes an on-ear component comprising a housing configured for placement on, in or about the wearer's ear. The on-ear component comprises a power source and a first interface coupled to the power source. The monitoring system also includes an in-ear component comprising a housing configured for deployment at least partially within an ear canal of the wearer. The in-ear component comprises a second interface configured to couple to and decouple from the first interface, a controller coupled to a memory, one or more physiologic sensors coupled to the controller and memory, and power management circuitry coupled to the controller. The power management circuitry comprises a wireless power receiver configured to receive power from the wireless powering arrangement. The power management circuitry is further configured to receive power from the power source of the on-ear component when the second interface is coupled to the first interface.

Embodiments are directed to a method of powering an ear-worn electronic monitoring system configured to be worn by a wearer. The method comprises powering, during wearer wakefulness, an in-ear component of the monitoring system using a power source of an on-ear component of the monitoring system. The method also comprises powering, during wearer sleep and with the on-ear component decoupled from the in-ear component, the in-ear component using a wireless power receiver of the in-ear component operatively coupled to a wireless powering arrangement. The method further comprises operating, during wearer sleep, the in-ear component using power received from the wireless powering arrangement via the wireless power receiver of the in-ear component.

Embodiments are directed to an ear-worn electronic monitoring system configured to be worn by a wearer and powered wirelessly at least during wearer sleep. The ear-worn electronic monitoring system comprises a first in-ear component comprising a housing configured for placement in the wearer's ear. The first in-ear component comprises a first wireless power receiver and a first interface coupled to the first wireless power receiver. A second in-ear component comprises a housing configured for deployment at least partially within an ear canal of the wearer and at a location of the ear closer to the wearer's ear drum than the first in-ear component. The second in-ear component comprises a second interface configured to couple to and decouple from the first interface, a controller coupled to a memory, one or more physiologic sensors coupled to the controller and memory, and power management circuitry coupled to the controller and configured to receive power from the first in-ear component via coupling between the first and second interfaces.

Embodiments are directed to an in-ear component configured to be worn by a wearer and powered wirelessly at least during wearer sleep via a wireless powering arrangement. The in-ear component comprises a housing configured for deployment at least partially within an ear canal of the wearer, a controller coupled to a memory, one or more physiologic sensors coupled to the controller and memory, and power management circuitry coupled to the controller and comprising a wireless power receiver configured to receive power from the wireless powering arrangement, wherein the in-ear component is devoid of a battery.

Embodiments are directed to an ear-worn electronic monitoring system configured to be worn by a wearer and powered wirelessly at least during wearer sleep. The ear-worn electronic monitoring system comprises a wireless powering arrangement comprising a power transmitter and an in-ear component. The in-ear component comprises a housing configured for deployment at least partially within an ear canal of the wearer, a controller coupled to a memory, one or more physiologic sensors coupled to the controller and memory, and power management circuitry coupled to the controller and comprising a wireless power receiver configured to receive power from the wireless powering arrangement, wherein the in-ear component is devoid of a battery.

Embodiments are directed to an ear-worn electronic monitoring system configured to be worn by a wearer and powered for use at least during wearer sleep. The ear-worn electronic monitoring system includes an on-ear component comprising a housing configured for placement on, in or about the wearer's ear. The on-ear component comprises a power source and a first interface coupled to the power source. An in-ear component of the monitoring system comprises a housing configured for deployment at least partially within an ear canal of the wearer. The in-ear component comprises a second interface configured to couple to and decouple from the first interface, a controller coupled to a memory, one or more physiologic sensors coupled to the controller and memory, and power management circuitry coupled to the controller and configured to receive power from the on-ear component via a connection between the first and second interfaces in a coupled mode. The on-ear component and the in-ear component are configured for deployment and cooperative operation in the coupled mode during wakefulness of the wearer. The in-ear component is configured for deployment and operation without the on-ear component in a decoupled mode during wearer sleep.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
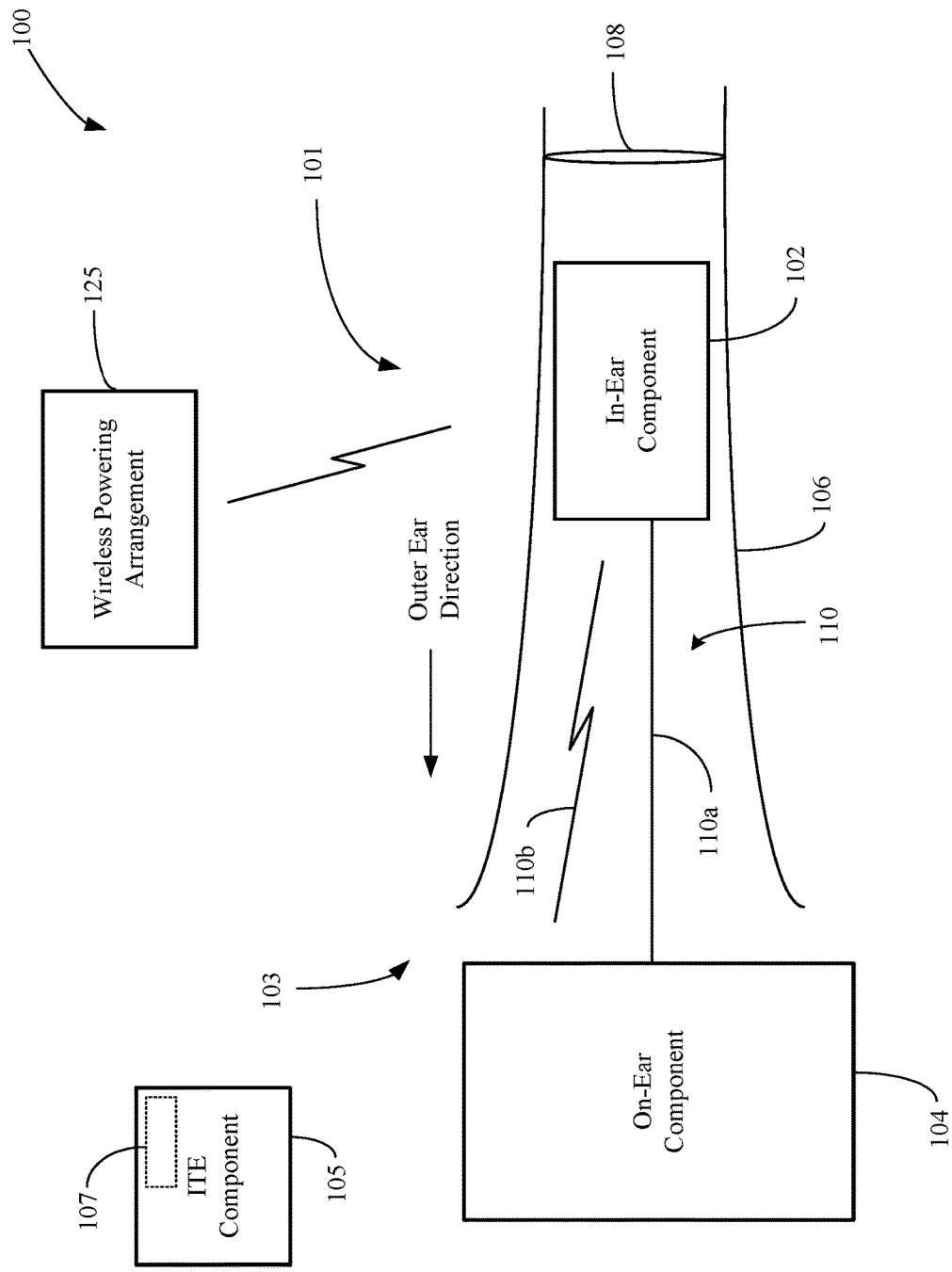
FIG. 1 illustrates an ear-worn electronic monitoring system in accordance with any of the embodiments disclosed herein.

Embodiments of the disclosure are directed to an ear-worn electronic system comprising an in-ear electronic device, referred to herein as an in-ear component, and a wireless powering arrangement configured to wirelessly supply power to the in-ear component. The in-ear component is configured for deployment at least partially within the wearer's ear, such as at least partially within an ear canal of the wearer's ear. The ear-worn electronic system can also include an on-ear electronic component, referred to herein as an on-ear component. The on-ear component is configured for placement on, in or about the wearer's ear and at a location which is spaced apart from the in-ear component in an outer ear direction. The on-ear component includes a power source which is used to supply power to the in-ear component for operation when the on-ear component is deployed on, in or about the wearer's ear.

The in-ear component refers to the device positioned closest to the wearer's ear drum, and the on-ear component refers to the device positioned furthest away from the wearer's ear drum when the in-ear and on-ear components are deployed relative to one of the wearer's ears. As such, the on-ear component is deployed at a location of the wearer's ear which is further from the wearer's ear drum in an outer ear direction relative to a location of the in-ear component during use at one of the wearer's ears. The in-ear component can be configured for deployment at least partially or entirely within the wearer's ear canal. The on-ear component can be configured for deployment entirely externally of the ear (e.g., beyond the outer ear such as behind the ear) or at least partially externally of the ear. The on-ear component can be configured for deployment at least partially within the outer ear, such as from the helix to the ear canal (e.g., the concha cymba, concha cavum) and can extend up to or into the ear canal.

According to a representative use scenario, the in-ear component is configured to receive power supplied by the wireless powering arrangement for operation in a wearer's ear during sleep. According to another representative use scenario, the in-ear component is configured to receive power supplied by the on-ear component for operation in the wearer's ear during wearer wakefulness. According to a further representative use scenario, the in-ear component is configured to receive power supplied by the wireless powering arrangement for operation in the wearer's ear during sleep, and further configured to receive power supplied by the on-ear component for operation in the wearer's ear during wearer wakefulness.

An ear-worn electronic system is configured for use with one ear of a wearer, such as the left ear or the right ear. In a representative implementation, an ear-worn electronic system comprising an in-ear component and an on-ear component can be configured for deployment in/at a wearer's left ear or the wearer's right ear. Two ear-worn electronic systems can be configured for use with both ears of a wearer, such that a first ear-worn electronic system is configured for use with one of the wearer's two ears and a second ear-worn electronic system is configured for use with the other of the wearer's two ears. In another representative implementation, a first ear-worn electronic system comprising a first in-ear component and a first on-ear component can be configured for deployment in/at a wearer's left ear. A second ear-worn electronic system comprising a second in-ear component and a second on-ear component can be configured for deployment in/at a wearer's right ear.

According to any of the embodiments disclosed herein, the in-ear component can be configured for prolonged deployment in a wearer's ear. For example, the in-ear component can be configured for continuous or nearly-continuous deployment in a wearer's ear (e.g., round-the-clock or substantially round-the-clock deployment within the wearer's ear). According to any of the embodiments disclosed herein, the in-ear component can be configured for deployment in a wearer's ear during a span of time that includes the wearer's sleep. According to any of the embodiments disclosed herein, the in-ear component can be configured for deployment in a wearer's ear during a span of time which includes both wakefulness of the wearer and the wearer's sleep (e.g., the entire duration of the wearer's sleep and some, most or all of the duration of wearer wakefulness).

In the context of any of the in-ear component deployment scenarios described herein, the on-ear component is configured to be deployed at, in or on the wearer's ear at a location proximal of the in-ear component in an outer ear direction. The on-ear component is configured for intermittent deployment at the wearer's ear relative to continuous or nearly-continuous deployment of the in-ear component in the wearer's ear. In accordance with any of the embodiments disclosed herein, the on-ear component can be configured for deployment at the wearer's ear during wakefulness of the wearer. For example, the on-ear component can be configured to be deployed at the wearer's ear during wakefulness of the wearer, and the in-ear component can be configured to be deployed in the wearer's ear during both wakefulness of the wearer and the wearer's sleep.

An ear-worn electronic device of the present disclosure refers to a wide variety of in-ear components configured to receive power wirelessly from a wireless powering arrangement. An ear-worn electronic system of the present disclosure refers to a wide variety of systems comprising an in-ear component and an on-ear component, such that the in-ear component is configured to receive power wirelessly from a wireless powering arrangement (e.g., during sleep) and to receive power from the on-ear component (e.g., during wakefulness). In-ear components include, but are not limited to, in-the-canal (ITC), completely-in-the-canal (CIC), and invisible-in-canal (IIC) type devices. On-ear components include, but are not limited to, behind-the-ear (BTE), in-the-ear (ITE), and receiver-in-canal (MC) type devices. The in-ear and on-ear components can be implemented as any combination of the above-listed devices. For example, the in-ear and on-ear components, when detachably coupled to one another, can have a configuration similar to that of a receiver-in-canal (MC) or receiver-in-the-ear (RITE) type device, with the in-ear component comprising components (e.g., sensors) in addition to, or to the exclusion of, a receiver or speaker. By way of further example, a representative on-ear component can be configured as a BTE device, in part, and ITE device, in part. A representative in-ear component can be configured as a CIC device, in part, and in ITE type device, in part. The on-ear component can be implemented as another type of hearable, such as a wearable earphones, headphone, or earbud.

In accordance with any of the embodiments disclosed herein, the ear-worn electronic system can be implemented as a physiologic (e.g., biometric) monitoring system. The in-ear component can include one or more physiologic sensors configured to sense one or more physiologic signals of the wearer. Additionally, or alternatively, the in-ear component can include one or more physiologic sensors configured to measure one or more physiologic conditions or states of the wearer.

In accordance with any of the embodiments disclosed herein, the ear-worn electronic system can be implemented as a physiologic (e.g., biometric) monitoring and hearing assistance system. The term hearing assistance system of the present disclosure refers to a wide variety of ear-level electronic devices that can aid a person with impaired hearing. The term hearing assistance system also refers to a wide variety of ear-level electronic devices that can produce optimized or processed sound for persons with normal hearing. For example, a hearing assistance system of the present disclosure can be implemented as a hearing aid system, in which in-ear and on-ear components are configured to operate as a hearing aid. A hearing assistance system comprising in-ear and on-ear components can be configured to receive streaming audio (e.g., digital audio data or files) from an electronic or digital source. Representative electronic/digital sources (e.g., accessory devices) include an assistive listening system, a streaming device (e.g., a TV streamer or audio streamer), a radio, a smartphone, a laptop, a cell phone/entertainment device (CPED) or other electronic device that serves as a source of digital audio data, control and/or settings data or commands, and/or other types of data files. A hearing assistance system comprising in-ear and on-ear components can be configured to effect bi-directional communication (e.g., wireless communication) of data with an external source, such as a remote server via the Internet or other communication infrastructure.

In accordance with any of the embodiments disclosed herein, an ear-worn electronic system can be implemented as a health, medical, and/or lifestyle monitoring system, and can include or exclude a hearing assistance system capability. The in-ear component includes one or more sensors. In some embodiments, the in-ear component and the on-ear component include one or more sensors. The one or more sensors include, but are not limited to, an EKG or ECG sensor, a pulse oximeter (e.g., $SpO_2$ sensor), a respiration sensor, a temperature sensor (e.g., for measuring core body temperature), a glucose sensor, an EEG sensor, an EMG sensor, an EOG sensor, a blood pressure sensor, and a galvanic skin response (e.g., electrodermal activity) sensor.

According to any of the embodiments disclosed herein, one or both of the in-ear and on-ear components can include one or more positional and/or motion sensors, such as one or more of accelerometers, gyros, magnetometers, and geo-location sensors. For example, a positional sensor and/or a motion sensor of one or both of the in-ear and on-ear components can be implemented to include one or more of a multi-axis (e.g., 9-axis) sensor, an IMU (inertial measurement unit), and an onboard GPS or an external GPS (e.g., a GPS of a smartphone communicatively linked to the ear-worn electronic system via a BLE link). A suitable IMU is disclosed in commonly owned U.S. Pat. No. 9,848,273, which is incorporated herein by reference. Typically, the on-ear component is configured to include a geo-location sensor due to size limitations of the in-ear component. For purposes of convenience, and not of limitation, the term positional sensor is used herein to refer to a positional sensor, a motion sensor, or a combination of positional and motion sensors.

According to any of the embodiments disclosed herein, the in-ear component of an ear-worn electronic system can be configured to be worn by the wearer while the wearer is sleeping. The in-ear component can include one or more sensors configured to provide the wearer and/or the wearer's caregiver/clinician with information about the wearer's sleep patterns, cardiac, pulmonary, and/or brain activity during sleep, potential sleep-related health issues (e.g., sleep disordered breathing, such as central or obstructive sleep apnea), and other physiologic and lifestyle information. The in-ear component can be configured to provide continued physiologic monitoring of the wearer during wearer wakefulness.

According to any of the embodiments disclosed herein, the in-ear component can be configured as both a sleep and/or biometric monitoring device operative during wearer sleep and a hearing device during wakefulness of the wearer. In applications where the in-ear component is deployed for a prolonged period (e.g., during periods of both sleep and wakefulness; round- or nearly round-the clock deployment), the in-ear component is configured to receive power wirelessly from a wireless powering arrangement for operation during sleep and to receive power from an on-ear component via a wired or wireless link for operation during wakefulness.

According to any of the embodiments disclosed herein, the on-ear component includes a rechargeable power source, such as a lithium-ion or other rechargeable battery. The on-ear component includes a power source and power delivery circuitry configured to supply power to the in-ear component, which typically is devoid of a power source (e.g., no rechargeable or conventional battery). In some embodiments, the in-ear component can include a rechargeable power source with a limited capacity which serves as a backup power source in the case of failed, interrupted or insufficient reception of power from the wireless powering arrangement. For example, the rechargeable power source of the in-ear component can have a capacity which provides for operation of the in-ear component during only a portion of the wearer's sleep (e.g., up to about one, two or three hours) in the case of failed, interrupted or insufficient reception of power from the wireless powering arrangement. Limiting the capacity of the rechargeable power source provides for an in-ear component having a relatively small size needed for deployment entirely of at least partially within the ear canal of the wearer's ear. In some embodiments, the rechargeable power source of one or both of the in-ear and on-ear components can include a supercapacitor, exclusive of or in addition to a rechargeable battery. In some embodiments described herein, the in-ear component includes a rechargeable battery, which is charged by the on-ear component, and excludes a wireless power receiver.

In addition to one or more sensors (e.g., physiologic and/or positional sensors), the in-ear component can include an audio processing facility (e.g., components of a typical hearing assistance device, e.g., a hearing aid, including a microphone, a receiver or speaker, an audio signal processing unit, and memory). For example, the in-ear component can include at least a microphone(s), a receiver/speaker, and audio processing circuitry which can be useful for environmental awareness, alerting the wearer to dangers and alarms, using the in-ear component(s) as a tinnitus masker, and to provide hearing aid-type functionality in the morning when the wearer first gets up, but before he or she has connected the on-ear component(s) to the in-ear component(s).

By way of further example, the in-ear component can be configured to provide a soothing background noise while the wearer is going to sleep. The in-ear component can be configured to provide an audio alert to the wearer in case the wearer's attention is needed (e.g., a crying baby, a smoke alarm, a carbon dioxide sensor alarm). The in-ear component can provide an audio alert that serves as an alarm clock. The in-ear component can be configured to switch to a low-power mode during wearer sleep, which can involve disabling of audio amplification and/or audio output so as not to awaken the wearer during sleep. In other configurations, the in-ear component comprises one or more sensors (e.g., physiologic and/or positional sensors) and is devoid of an audio processing facility.

In some configurations, a "sleep monitoring mode" can be triggered by a combination of the in-ear and on-ear components being separated from one other along with one or more of the following events. A representative event can be a manual indication by the wearer of the ear-worn electronic system that he/she is going to sleep now (e.g., via a push button, capacitive switch, toggle switch, tapping the in-ear component, etc.). A representative event can be an indication through an app (e.g., on a smartphone) or a voice recognition command (e.g., saying, "sleep" to the ear-worn electronic system). A representative event can involve a time buffer, such as a countdown timer. For example, it can be assumed that a wearer of the ear-worn electronic system gets in bed within X minutes of disconnecting the in-ear and on-ear components, where X can be configured by the wearer. A representative event can be sensing that the wearer is lying down in response to signals produced by a positional sensor(s) of the in-ear component. A representative event can be sensing that the wearer is asleep in response to biometric indicators determined using a physiologic sensor(s) of the in-ear component.

The on-ear component includes components that cooperate to supply power to the in-ear component when the on-ear component is deployed at the wearer's ear. For example, the on-ear component can include a power source and power supply circuitry configured to deliver power to power management circuitry of the in-ear component. In embodiments in which the in-ear component includes a rechargeable power source, the on-ear component includes components that cooperate to charge the rechargeable power source of the in-ear component. In such embodiments, the on-ear component includes a rechargeable power source, charging circuitry, and circuitry for establishing a charging link (wired or wireless) with charging circuitry of the in-ear component. In addition to these power delivery/charging components, the on-ear component can also include components of a typical hearing assistance device (e.g., hearing aid), such as those listed above. The on-ear component can comprise one or more sensors (e.g., physiologic and/or positional sensors), in addition to or to the exclusion of components of a typical hearing assistance device (e.g., hearing aid).

In accordance with a representative use scenario, the in-ear component is deployed at least partially within the wearer's ear canal for continuous or near-continuous operation, and the on-ear component is deployed proximal of the in-ear component in an outer ear direction (e.g., behind the ear) only during a period of wakefulness of the wearer. In this wakefulness configuration, the in-ear component is coupled to the on-ear component via a power link, which may be a wired or wireless link. During the period of wakefulness, the on-ear component supplies power to power management circuitry of the in-ear component via the power link, allowing the in-ear component to operate throughout the wakefulness period. Prior to the wearer's sleep, the on-ear component is separated from the in-ear component, removed from the wearer's ear, and placed in a charging unit, such that this decoupling of the two components terminates power delivery from the on-ear component to the in-ear component. During the wearer's sleep, the in-ear component remains deployed within the wearer's ear and is configured to wirelessly receive power from an external wireless powering arrangement, allowing the in-ear component to operate continuously during the wearer's sleep.

In a charging mode, such as during the wearer's sleep, minimally the battery of the on-ear component is charged. While charging, the on-ear component can be configured to sync data that has been stored in or acquired by the on-ear component throughout the day with one or more other devices, such as one or more computers, smartphones or cloud-based storage systems. In this scenario, data that the on-ear component transfers may have been received from the in-ear component when the two components were last connected. For example, a charging unit (desktop or portable) can be used to charge the on-ear component when disconnected from the in-ear component. The charging unit can include a processor and an input/output interface for receiving data stored in the on-ear component, which may include in-ear component data in addition to on-ear component data. The processor of the charging unit can be configured to analyze at least some of the data that it receives, or it may serve as a relay between the on-ear/in-ear components and one or more other computers/cloud-based storage systems. After the data is stored and analyzed, the results may be shared with the device manufacturer and/or the device wearer (e.g., via an app or a web site).

The transfer of data from the on-ear component to another device for analysis and storage can occur automatically whenever the on-ear component is resting in or coupled to the charging unit. Further, while the on-ear component is connected to the charging unit, the charging unit can push information to the on-ear component, which in turn, can push information to the in-ear component once they are reconnected. This information can include firmware updates or parameter changes, some of which may be recommendations based on an analysis of the wearer's data that were previously offloaded. Other parameter changes may be based on an analysis of data from a larger group of device wearers. In some configurations, communication between the in-ear and on-ear components is facilitated via a physical connection, examples of which are described herein. In other configurations, communication between the in-ear and on-ear components is facilitated via a wireless connection, examples of which are described herein.

This document discloses numerous embodiments, including but not limited to the following:

Aspect 1 is an ear-worn electronic monitoring system configured to be worn by a wearer and powered wirelessly at least during wearer sleep, the ear-worn electronic monitoring system comprising:
 an on-ear component comprising a housing configured for placement on, in or about the wearer's ear, the on-ear component comprising a power source and a first interface coupled to the power source; and
 an in-ear component comprising a housing configured for deployment at least partially within an ear canal of the wearer, the in-ear component comprising:
  a second interface configured to couple to and decouple from the first interface;
  a controller coupled to a memory;
  one or more physiologic sensors coupled to the controller and memory; and
  power management circuitry coupled to the controller and comprising a wireless power receiver configured to receive power from a wireless powering arrangement, the power management circuitry further configured to receive power from the power source of the on-ear component when the second interface is coupled to the first interface.

Aspect 2 is the system according to aspect 1, wherein:
 the on-ear component and the in-ear component are configured for deployment and cooperative operation in a coupled mode during wakefulness of the wearer; and
 the in-ear component is configured for deployment without the on-ear component in a decoupled mode during wearer sleep.

Aspect 3 is the system according to aspect 1 or aspect 2, wherein
 the power management circuitry is configured to receive power from the power source of the on-ear component when the second interface is coupled to the first interface; and
 the wireless power receiver is configured to wirelessly receive power from the wireless powering arrangement when the second interface is uncoupled from the first interface.

Aspect 4 is the system according to any of the preceding aspects, wherein the in-ear component is devoid of a battery.

Aspect 5 is the system according to any of aspect 1 through aspect 3, wherein the in-ear component comprises a rechargeable battery coupled to the power management circuitry and configured to serve as a backup power source in response to failed, interrupted or insufficient reception of power from the wireless powering arrangement.

Aspect 6 is the system according to any of the preceding aspects, wherein the second interface is configured for wired coupling to the first interface.

Aspect 7 is the system according to any of the preceding aspects, wherein one of the first and second interfaces is configured to receive an elongated electrical conductor arrangement of the other of the first and second interfaces.

Aspect 8 is the system according to any of the preceding aspects, wherein one of the first and second interfaces comprises an elongated connector configured to electrically and mechanically couple to and decouple from the other of the first and second interfaces.

Aspect 9 is the system according to any of the preceding aspects, wherein one of the first and second interfaces comprises an elongated electrical conductor arrangement configured for manual attachment to and manual detachment from the other of the first and second interfaces.

Aspect 10 is the system according to any of aspect 1 through aspect 5, wherein the second interface is configured to wirelessly couple to the first interface.

Aspect 11 is the system according to any of aspect 1 through aspect 5, wherein the first interface comprises a wireless powering arrangement configured to wirelessly couple power to the wireless power receiver of the power management circuitry.

Aspect 12 is the system according to any of aspect 1 through aspect 5, further comprising an in-the-ear (ITE) device comprising a battery and the wireless powering arrangement configured to wirelessly couple power to the wireless power receiver of the in-ear component during wearer sleep.

Aspect 13 is the system according to aspect 12, wherein:
 the on-ear component is configured to provide power to the in-ear component during wearer wakefulness; and
 the ITE device is configured to wirelessly couple power to the in-ear component during wearer sleep.

Aspect 14 is a system, comprising:
 a first ear-worn electronic monitoring system comprising the on-ear component and the in-ear component according to any of the preceding aspects configured for deployment at a first ear of the wearer; and
 a second ear-worn electronic monitoring system comprising the on-ear component and the in-ear component according to any of the preceding aspects configured for deployment at a second ear of the wearer.

Aspect 15 is the system according to any of the preceding aspects, wherein the in-ear component further comprises one or any combination of a wireless transmitter or transceiver, a speaker or receiver, a microphone or microphones, audio processing circuitry, and a controller or processor.

Aspect 16 is the system according to any of the preceding aspects, wherein the on-ear component further comprises one or any combination of a wireless transmitter or transceiver, a speaker or receiver, a microphone or microphones, audio processing circuitry, a controller or processor, and one or more physiologic sensors.

Aspect 17 is a system, comprising:
 a wireless powering arrangement comprising a power transmitter; and
 an ear-worn electronic monitoring system configured to be worn by a wearer and powered wirelessly at least during wearer sleep by the wireless powering arrangement, the ear-worn electronic monitoring system comprising:

an on-ear component comprising a housing configured for placement on, in or about the wearer's ear, the on-ear component comprising a power source and a first interface coupled to the power source; and an in-ear component comprising a housing configured for deployment at least partially within an ear canal of the wearer, the in-ear component comprising:
- a second interface configured to couple to and decouple from the first interface;
- a controller coupled to a memory;
- one or more physiologic sensors coupled to the controller and memory; and
- power management circuitry coupled to the controller and comprising a wireless power receiver configured to receive power from the wireless powering arrangement, the power management circuitry further configured to receive power from the power source of the on-ear component when the second interface is coupled to the first interface.

Aspect 18 is the system according to aspect 17, wherein the wireless powering arrangement is configured as a near-field wireless powering arrangement.

Aspect 19 is the system according to aspect 17, wherein the wireless powering arrangement is configured as a far-field wireless powering arrangement.

Aspect 20 is the system according to any of aspect 17 through aspect 19, wherein the wireless powering arrangement comprises a head-worn device configured to support the power transmitter.

Aspect 21 is the system according to aspect 20, wherein the head-worn device comprises a battery configured to supply power for the wireless powering arrangement.

Aspect 22 is the system according to aspect 20, wherein the head-worn device comprises a headband.

Aspect 23 is the system according to aspect 20, wherein the head-worn device comprises a sleep mask configured to cover the wearer's eyes.

Aspect 24 is the system according to aspect 20, wherein the head-worn device comprises a mask of an apparatus configured to deliver a sleep disordered breathing therapy.

Aspect 25 is the system according to any of aspect 17 through aspect 24, wherein the power transmitter of the wireless powering arrangement incorporates or is coupled to an array of antennas configured to focus radio frequency waves on the wireless power receiver of the in-ear component.

Aspect 26 is the system according to aspect 25, wherein:
- the in-ear component comprises a first wireless transmitter or transceiver configured to communicate power transfer information to a wireless receiver or transceiver of the wireless powering arrangement; and
- the wireless powering arrangement is configured to steer the array of antennas to enhance reception of the radio frequency waves by the wireless charging receiver in response to the power transfer information received from the in-ear component.

Aspect 27 is the system according to any of aspect 17 through aspect 26, wherein:
- the on-ear component and the in-ear component are configured for deployment and cooperative operation in a coupled mode during wakefulness of the wearer; and
- the in-ear component is configured for deployment without the on-ear component in a decoupled mode during wearer sleep.

Aspect 28 is the system according to any of aspect 17 through aspect 27, wherein the power management circuitry is configured to receive power from the power source of the on-ear component when the second interface is coupled to the first interface; and the wireless power receiver is configured to wirelessly receive power from the wireless powering arrangement when the second interface is uncoupled from the first interface.

Aspect 29 is the system according to any of aspect 17 through aspect 28, wherein the in-ear component is devoid of a battery.

Aspect 30 is the system according to any of aspect 17 through aspect 28, wherein the in-ear component comprises a rechargeable battery coupled to the power management circuitry and configured to serve as a backup power source in response to failed, interrupted or insufficient reception of power from the wireless powering arrangement.

Aspect 31 is the system according to any of aspect 17 through aspect 30, wherein the second interface is configured for wired coupling to the first interface.

Aspect 32 is the system according to any of aspect 17 through aspect 31, wherein one of the first and second interfaces is configured to detachably receive an elongated electrical conductor arrangement of the other of the first and second interfaces.

Aspect 33 is the system according to any of aspect 17 through aspect 32, wherein one of the first and second interfaces comprises an elongated connector configured to electrically and mechanically couple to and decouple from the other of the first and second interfaces.

Aspect 34 is the system according to any of aspect 17 through aspect 33, wherein one of the first and second interfaces comprises an elongated electrical conductor arrangement configured for manual attachment to and manual detachment from the other of the first and second interfaces.

Aspect 35 is the system according to any of aspect 17 through aspect 30, wherein the second interface is configured to wirelessly couple to the first interface.

Aspect 36 is the system according to any of aspect 17 through aspect 30, wherein the first interface comprises a wireless powering arrangement configured to wirelessly couple power to the wireless power receiver of the power management circuitry.

Aspect 37 is the system according to any of aspect 17 through aspect 30, further comprising an in-the-ear (ITE) device comprising a battery and the wireless powering arrangement configured to wirelessly couple power to the wireless power receiver of the in-ear component during wearer sleep.

Aspect 38 is the system according to aspect 37, wherein:
- the on-ear component is configured to provide power to the in-ear component during wearer wakefulness; and
- the ITE device is configured to wirelessly couple power to the in-ear component during wearer sleep.

Aspect 39 is a system, comprising:
- a first ear-worn electronic monitoring system comprising the on-ear component and the in-ear component according to any of aspect 17 through aspect 38 configured for deployment at a first ear of the wearer; and
- a second ear-worn electronic monitoring system comprising the on-ear component and the in-ear component according to any of aspect 17 through aspect 38 configured for deployment at a second ear of the wearer.

Aspect 40 is the system according to any of aspect 17 through aspect 39, wherein the in-ear component further comprises one or any combination of a wireless transmitter or transceiver, a speaker or receiver, a microphone or microphones, audio processing circuitry, and a controller or processor.

Aspect 41 is the system according to any of aspect 17 through aspect 40, wherein the on-ear component further comprises one or any combination of a wireless transmitter or transceiver, a speaker or receiver, a microphone or microphones, audio processing circuitry, a controller or processor, and one or more physiologic sensors.

Aspect 42 is the system according to any of the preceding aspects, wherein the memory is configured to store one or more physiologic signals or sensed physiologic conditions of the wearer generated or acquired by the one or more physiologic sensors.

Aspect 43 is the system according to aspect 42, wherein the in-ear component comprises a wireless transceiver configured to communicate physiologic information stored in the memory to a wireless transceiver of the on-ear component or to an external device or system.

Aspect 44 is the system according to aspect 42, wherein the on-ear component comprises a memory configured to store the one or more physiologic signals or sensed physiologic conditions of the wearer received from the memory of the in-ear component.

Aspect 45 is the system according to aspect 42, wherein:
  the on-ear component comprises a memory and one or more physiologic sensors; and
  the memory of the on-ear component is configured to store one or more physiologic signals or sensed physiologic conditions of the wearer generated or acquired by the one or more physiologic sensors of the on-ear component.

Aspect 46 is the system according to aspect 45, wherein the memory of the on-ear component is configured to store the one or more physiologic signals or sensed physiologic conditions of the wearer received from the memory of the in-ear component.

Aspect 47 is the system according to any of aspect 43 through aspect 46, wherein the on-ear component comprises a wireless transceiver configured to communicate physiologic information stored in the memory of the on-ear component to an external device or system.

Aspect 48 is a method of powering an ear-worn electronic monitoring system configured to be worn by a wearer, the method comprising:
  powering, during wearer wakefulness, an in-ear component of the monitoring system using a power source of an on-ear component of the monitoring system;
  powering, during wearer sleep and with the on-ear component decoupled from the in-ear component, the in-ear component using a wireless power receiver of the in-ear component operatively coupled to a wireless powering arrangement; and
  operating, during wearer sleep, the in-ear component using power received from the wireless powering arrangement via the wireless power receiver of the in-ear component.

Aspect 49 is the method according to aspect 48, wherein powering the in-ear component during wearer wakefulness comprises supplying power from the power source of the on-ear component to power management circuitry of the in-ear component via a wired connection.

Aspect 50 is the method according to aspect 48, wherein powering the in-ear component during wearer wakefulness comprises wirelessly supplying power from the power source of the on-ear component to the wireless power receiver in-ear component.

Aspect 51 is the method according to any of aspect 48 through aspect 50, comprising:
  sensing one or more physiologic parameters or conditions of the wearer using one or more sensors of the in-ear component; and
  storing physiologic data indicative of the sensed one or more physiologic parameters or conditions of the wearer in a memory of the in-ear component.

Aspect 52 is the method according to any of aspect 48 through aspect 50, comprising:
  sensing, during wearer sleep, one or more physiologic parameters or conditions of the wearer using one or more sensors of the in-ear component; and
  storing, during wearer sleep, physiologic data indicative of the sensed one or more physiologic parameters or conditions of the wearer in a memory of the in-ear component.

Aspect 53 is the method according to any of aspect 48 through aspect 52, comprising:
  sensing, during wearer wakefulness, one or more physiologic parameters or conditions of the wearer using one or more sensors of the on-ear component; and
  storing physiologic data indicative of the sensed one or more physiologic parameters or conditions of the wearer in a memory of the on-ear component.

Aspect 54 is the method according to any of aspect 48 through aspect 50, comprising:
  sensing one or more physiologic parameters or conditions of the wearer using one or more sensors of the in-ear component;
  storing physiologic data indicative of the sensed one or more physiologic parameters or conditions of the wearer in a memory of the in-ear component;
  communicating physiologic data stored in the memory of the in-ear component to the on-ear component with the on-ear component coupled to the in-ear component; and
  storing the physiologic data communicated from the in-ear component in a memory of the on-ear component.

Aspect 55 is the method according to any of aspect 48 through aspect 50, comprising:
  sensing, during wearer sleep, one or more physiologic parameters or conditions of the wearer using one or more sensors of the in-ear component;
  storing, during wearer sleep, physiologic data indicative of the sensed one or more physiologic parameters or conditions of the wearer in a memory of the in-ear component;
  communicating, during wearer wakefulness, the physiologic data stored in the memory of the in-ear component to the on-ear component with the on-ear component coupled to the in-ear component; and
  storing the physiologic data communicated from the in-ear component in a memory of the on-ear component.

Aspect 56 is the method according to any of aspect 51 through aspect 55, comprising wirelessly communicating the physiologic data stored in the memory of the in-ear component to a wireless transceiver of the on-ear component or to an external device or system.

Aspect 57 is the method according to any of aspect 52 through aspect 55, comprising wirelessly communicating the physiologic data stored in the memory of the on-ear component to an external device or system.

Aspect 60 is an ear-worn electronic monitoring system configured to be worn by a wearer and powered wirelessly at least during wearer sleep, the ear-worn electronic monitoring system comprising:

a first in-ear component comprising a housing configured for placement in the wearer's ear, the first in-ear component comprising a first wireless power receiver and a first interface coupled to the first wireless power receiver; and a second in-ear component comprising a housing configured for deployment at least partially within an ear canal of the wearer and at a location of the ear closer to the wearer's ear drum than the first in-ear component, the second in-ear component comprising:

a second interface configured to couple to and decouple from the first interface;

a controller coupled to a memory;

one or more physiologic sensors coupled to the controller and memory; and power management circuitry coupled to the controller and configured to receive power from the first in-ear component via coupling between the first and second interfaces.

Aspect 61 is the system of aspect 60, wherein the first in-ear component comprises a power source operatively coupled to the first interface.

Aspect 62 is the system of aspect 60 or aspect 61, wherein the first in-ear component is an in-the-ear (ITE) device.

Aspect 63 is an in-ear component configured to be worn by a wearer and powered wirelessly at least during wearer sleep via a wireless powering arrangement, the in-ear component comprising:

a housing configured for deployment at least partially within an ear canal of the wearer;

a controller coupled to a memory;

one or more physiologic sensors coupled to the controller and memory; and power management circuitry coupled to the controller and comprising a wireless power receiver configured to receive power from the wireless powering arrangement, wherein the in-ear component is devoid of a battery.

Aspect 64 is an ear-worn electronic monitoring system configured to be worn by a wearer and powered wirelessly at least during wearer sleep, the ear-worn electronic monitoring system comprising:

a wireless powering arrangement comprising a power transmitter; and an in-ear component comprising:

a housing configured for deployment at least partially within an ear canal of the wearer;

a controller coupled to a memory;

one or more physiologic sensors coupled to the controller and memory; and power management circuitry coupled to the controller and comprising a wireless power receiver configured to receive power from the wireless powering arrangement, wherein the in-ear component is devoid of a battery.

Aspect 65 is an ear-worn electronic monitoring system configured to be worn by a wearer and powered for use at least during wearer sleep, the ear-worn electronic monitoring system comprising:

an on-ear component comprising a housing configured for placement on, in or about the wearer's ear, the on-ear component comprising a power source and a first interface coupled to the power source; and an in-ear component comprising a housing configured for deployment at least partially within an ear canal of the wearer, the in-ear component comprising:

a second interface configured to couple to and decouple from the first interface;

a controller coupled to a memory;

one or more physiologic sensors coupled to the controller and memory; and power management circuitry coupled to the controller and configured to receive power from the on-ear component via a connection between the first and second interfaces in a coupled mode, wherein:

the on-ear component and the in-ear component are configured for deployment and cooperative operation in the coupled mode during wakefulness of the wearer; and the in-ear component is configured for deployment and operation without the on-ear component in a decoupled mode during wearer sleep.

FIG. 1 illustrates an ear-worn electronic monitoring system 100 in accordance with any of the embodiments disclosed herein. The monitoring system 100 includes a wireless powering arrangement 125 and an ear-worn electronic system 101 shown in a deployed configuration at a wearer's ear 103. The monitoring system 100 is configured to operate in primarily two modes—a wakefulness mode and a sleep mode. In the wakefulness mode, the operative elements of monitoring system 100 include the in-ear component 102 and the on-ear component 104. In the sleep mode, the operative elements of monitoring system 100 include the in-ear component 102 and the wireless powering arrangement 125.

In FIG. 1, the ear-worn electronic system 101 is shown deployed in a connected (e.g., operatively coupled) configuration appropriate for use during wakefulness of the wearer. In the wakefulness mode of operation, the system 101 includes the in-ear component 102 operatively coupled to the on-ear component 104. In the wakefulness mode, power required for in-ear component operation is received from the on-ear component 104, in which case the wireless powering arrangement 125 is typically not implicated or operative. In the wakefulness mode, it is assumed that the wearer of the system 101 is, or can be, ambulatory and able to move well beyond the range of the wireless powering arrangement 125. In the sleep mode of operation, the system 101 includes the in-ear component 102 operatively coupled to the wireless powering arrangement 125, in which case the on-ear component 104 is typically not implicated or operative. For example, the on-ear component 104 can be placed in a charging unit during the period of sleep mode of operation.

As previously discussed, the in-ear component 102 is configured for placement at least partially within an ear canal 106 of the wearer's ear 103. In some configurations, the in-ear component 102 is configured for placement completely within the wearer's ear-canal 106. The on-ear component 104 is configured for placement at or about the wearer's ear 103. In some configurations, the on-ear component 104 can be configured for placement entirely externally of the wearer's ear 103, such as behind the wearer's ear 103. In other configurations, the on-ear component 104 can be configured for placement at least partially externally of the ear. For example, the on-ear component 104 can be configured for deployment at least partially within the outer ear, such as from the helix to the ear canal (e.g., the concha cymba, concha cavum) and can extend up to or into the ear canal 106. As is shown in FIG. 1, the in-ear component 102 is positioned closest to the wearer's eardrum 108, and the on-ear component 104 is positioned furthest away from the eardrum 108 in the outer ear direction.

According to some embodiments, the monitoring system 100 includes the in-ear component 102, the on-ear component 104, the wireless powering arrangement 125, and an in-the-ear (ITE) device 105. The ITE device 105 has a size and shape that can be deployed comfortably within the wearer's ear 103 during sleep (e.g., with the ear 103 resting against a pillow). For example, the ITE device 105 can have a housing that fits within the wearer's concha with little or no portion extending beyond or outside of the outer ear. The on-ear component 104 is deployed during wearer wakefulness and configured to supply power to the in-ear component 102 as previously described. Prior to sleep, the on-ear component 104 is removed from the wearer's ear and placed in a charging unit. The ITE device 105 is deployed in the wearer's ear 103 and operatively coupled to the in-ear component 102 via a wired or wireless link. The ITE device 105 typically has a housing larger than that of the in-ear component 102, and can accommodate a larger and more efficient wireless charging antenna 107 relative to that of the in-ear component 102 described in previous configurations.

In this embodiment, the in-ear component 102 need not include a wireless charging antenna (e.g., a wireless power receiver), but may instead receive power from the ITE device 105 during the sleep mode of operation (typically via a wired link, but may instead be configured as a wireless link). The ITE device 105 may also include a back-up battery, which may be a rechargeable or conventional battery. The battery of the ITE device 105 may have a limited capacity (e.g., insufficient capacity to power the in-ear component 102 continuously through 7-9 hours of wearer sleep) and can be configured to serve as a backup power source in response to failed, interrupted or insufficient reception of power from the wireless powering arrangement 125. Alternatively, the battery of the ITE device 105 may have a capacity sufficient to supply continuous power to the in-ear component 102 for the entire duration of the wearer sleep (e.g., 7-9 hours). After a period of sleep, the wearer can remove the ITE device 105, place the ITE device in a charging unit, and redeploy the on-ear component 104 in or on the wearer's ear, allowing the monitoring system 100 to operate in the wakefulness mode.

In the configuration shown in FIG. 1, the in-ear and on-ear components 102, 104 are coupled together via a link 110. In some configurations, the in-ear and on-ear components 102, 104 can be connected via a wired link 110a, such as link comprising a multiplicity of electrical conductors, and, optionally, optical fibers (e.g., for power delivery and/or data transfer). The wired link 110a can include a power link and a data link. In other configurations, the in-ear and on-ear components 102, 104 can be coupled via a wireless link 110b, such as an inductive link and/or a radio frequency link (e.g., a wireless power transmitter, receiver, and/or transceiver). In addition to power transmission, the link 110 can be configured to facilitate communication of various types of data and signals between the in-ear and on-ear components 102, 104.

Figure 2:
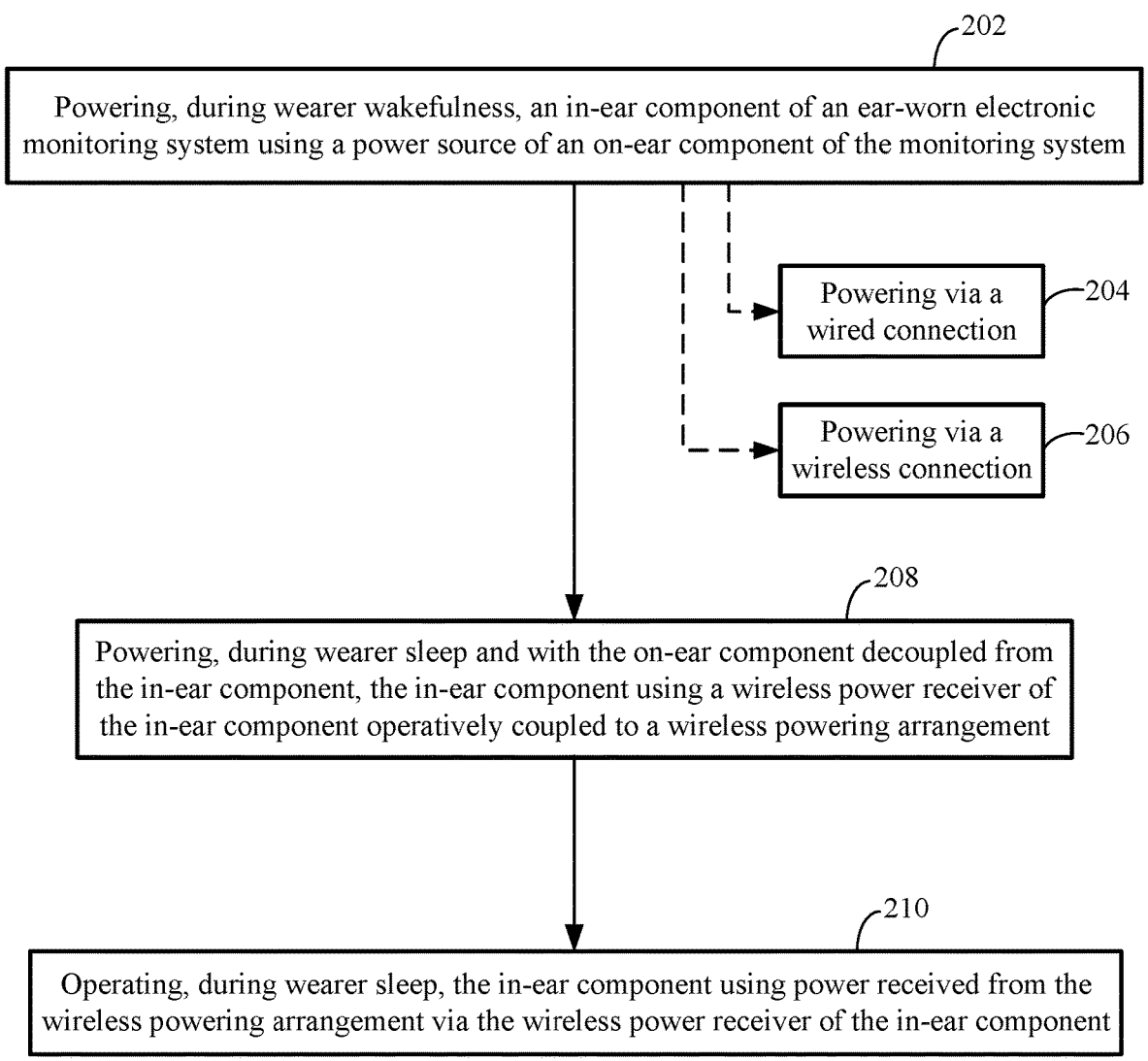
FIG. 2 illustrates a method implemented by an ear-worn electronic monitoring system in accordance with any of the embodiments disclosed herein.

FIG. 2 illustrates a method implemented by an ear-worn electronic monitoring system in accordance with various embodiments. The method shown in FIG. 2 involves powering 202, during wearer wakefulness, an in-ear component of an ear-worn electronic monitoring system using a power source of an on-ear component of the monitoring system. In some approaches, the method involves powering 204 the in-ear component via a wired connection between the in-ear component and the on-ear component. In other approaches, the method involves powering 206 the in-ear component via a wireless connection between the in-ear component and the on-ear component. The method also involves powering 208, during wearer sleep and with the on-ear component decoupled from the in-ear component, the in-ear component using a wireless power receiver of the in-ear component operatively coupled to a wireless powering arrangement. The wireless powering arrangement is an arrangement external of the monitoring system. The method further involves operating 210, during wearer sleep, the in-ear component using power received from the wireless powering arrangement via the wireless power receiver of the in-ear component.

Figure 3:
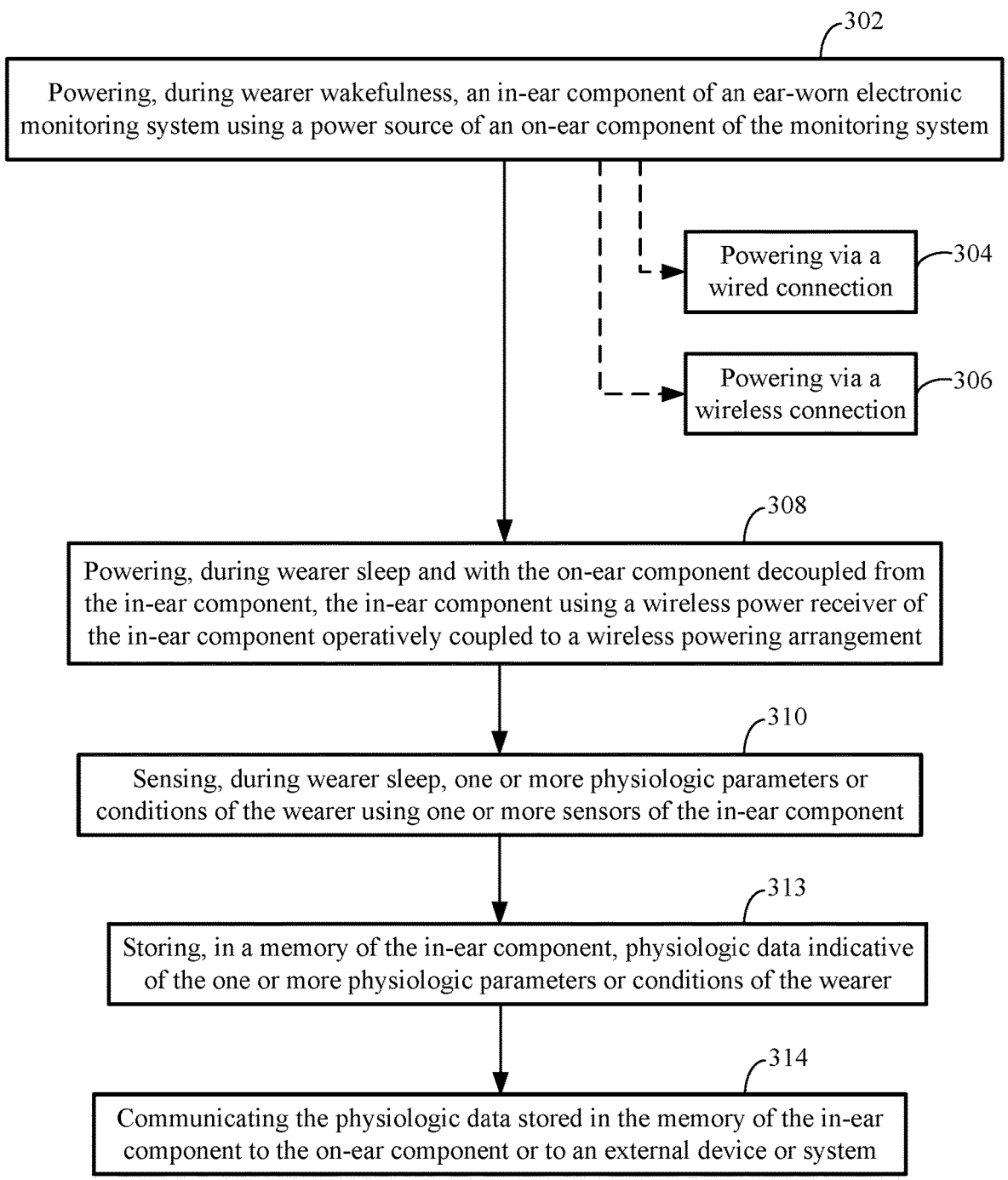
FIG. 3 illustrates a method implemented by an ear-worn electronic monitoring system in accordance with any of the embodiments disclosed herein.

FIG. 3 illustrates a method implemented by an ear-worn electronic monitoring system in accordance with various embodiments. The method shown in FIG. 3 involves powering 302, during wearer wakefulness, an in-ear component of an ear-worn electronic monitoring system using a power source of an on-ear component of the monitoring system. In some approaches, the method involves powering 304 the in-ear component via a wired connection between the in-ear component and the on-ear component. In other approaches, the method involves powering 306 the in-ear component via a wireless connection between the in-ear component and the on-ear component. The method also involves powering 308, during wearer sleep and with the on-ear component decoupled from the in-ear component, the in-ear component using a wireless power receiver of the in-ear component operatively coupled to a wireless powering arrangement. The method further involves sensing 310, during wearer sleep, one or more physiologic parameters or conditions of the wearer using one or more sensors of the in-ear component. The method involves storing 313, in a memory of the in-ear component, physiologic data indicative of the one or more physiologic parameters or conditions of the wearer. The method also involves communicating 314 the physiologic data stored in the memory of the in-ear component to the on-ear component or to an external device or system.

Figure 4:
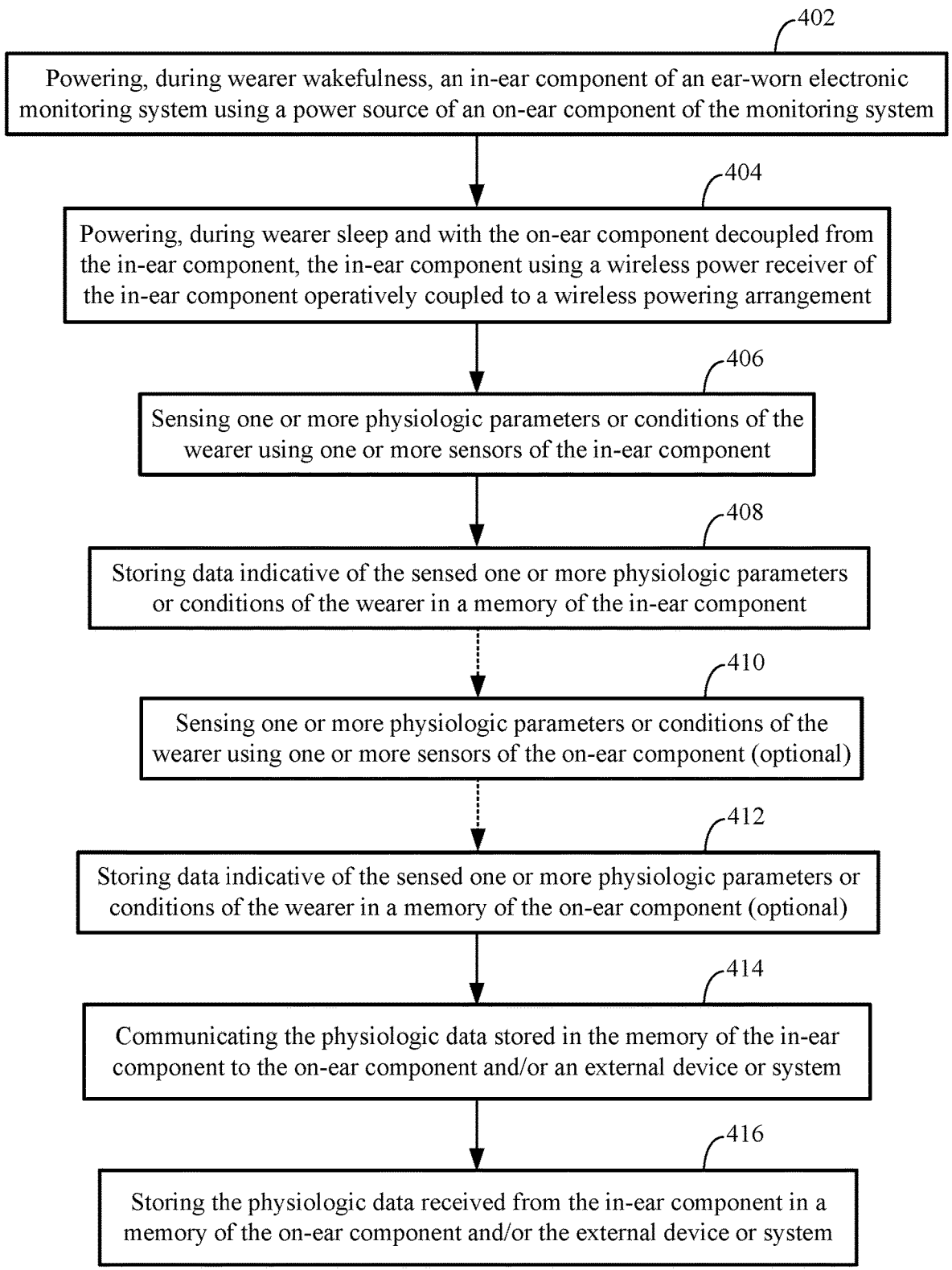
FIG. 4 illustrates a method implemented by an ear-worn electronic monitoring system in accordance with any of the embodiments disclosed herein.

FIG. 4 illustrates a method implemented by an ear-worn electronic monitoring system in accordance with various embodiments. The method shown in FIG. 4 involves powering 402, during wearer wakefulness, an in-ear component of the ear-worn electronic monitoring system using a power source of an on-ear component of the monitoring system. The method also involves powering 404, during wearer sleep and with the on-ear component decoupled from the in-ear component, the in-ear component using a wireless power receiver of the in-ear component operatively coupled to a wireless powering arrangement. The method involves sensing 406 one or more physiologic parameters or conditions of the wearer using one or more sensors of the in-ear component. The method also involves storing 408 data indicative of the sensed one or more physiologic parameters or conditions of the wearer in a memory of the in-ear component. The method can optionally involve sensing 410 one or more physiologic parameters or conditions of the wearer using one or more sensors of the on-ear component. The method can optionally involve storing 412 data indicative of the sensed one or more physiologic parameters or conditions of the wearer in a memory of the on-ear component. The method shown in FIG. 4 further involves communicating 414 the physiologic data stored in the memory of the in-ear component to the on-ear component and/or an external device or system. The method also involves storing 416 the physiologic data received from the in-ear component in a memory of the on-ear component and/or the external device or system.

Figure 5:
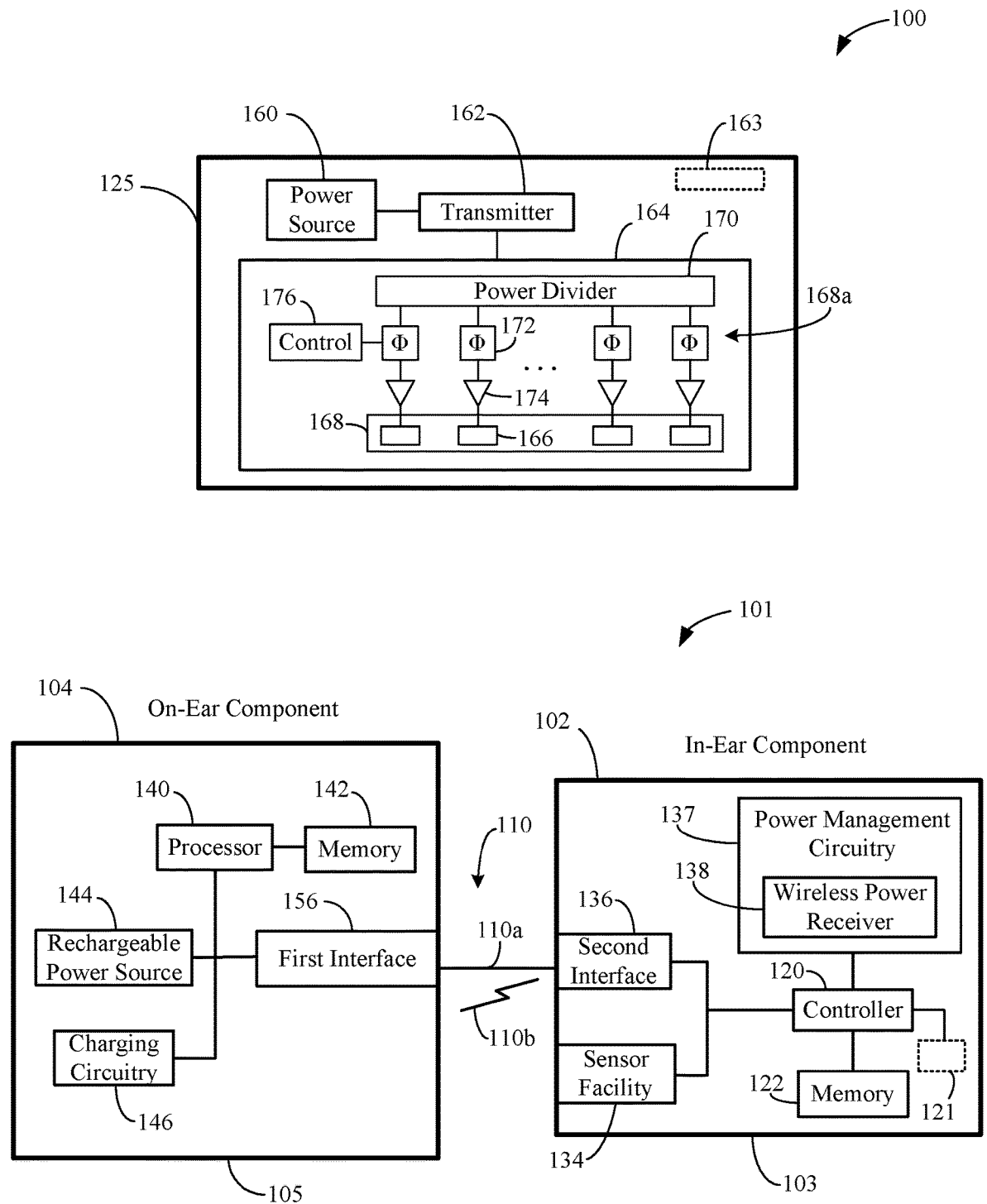
FIG. 5 illustrates an ear-worn electronic monitoring system in accordance with any of the embodiments disclosed herein.

FIG. 5 illustrates an ear-worn electronic monitoring system 100 in accordance with any of the embodiments disclosed herein. The monitoring system 100 includes an ear-worn electronic system 101 comprising an in-ear component 102 and an on-ear component 104. In the configuration shown in FIG. 5, the in-ear component 102 includes a housing 103 configured for placement partially or entirely within an ear canal of a wearer of the system 101. In some configurations, the shape of the housing 103 can be customized for the wearer's ear canal (e.g., based on a mold taken from the wearer's ear canal). In other configurations, the housing 103 can be constructed from pliant (e.g., semisoft) material that, when inserted into the wearer's ear canal, takes on the shape of the ear canal.

The in-ear component 102 includes a number of components that can vary depending on the configuration and functionality of the in-ear component 102 and that of the on-ear component 104. Typically, each of the various configurations of the in-ear component 102 includes a number of core components. In the representative embodiment shown in FIG. 5, for example, the core components of the in-ear component 102 include a controller 120 (e.g., a processor, a logic device, an FPGA, an ASIC, etc.) coupled to memory 122, power management circuitry 137 comprising a wireless power receiver 138, a second interface 136, and a sensor facility 134 coupled to the controller 120 and the memory 122.

In some embodiments, the in-ear component 102 is configured as a physiologic sensing device, and the sensor facility 134 comprises one or more physiologic sensors, representative examples of which are disclosed herein. The sensor facility 134 can include one or more positional sensors, representative examples of which are disclosed herein, in addition to, or exclusive of, one or more physiologic sensors. In other embodiments, the in-ear component 102 can be configured as a hearing device comprising one or more microphones and a speaker or receiver (e.g., see components shown in FIG. 6). In further embodiments, the in-ear component 102 can be configured as a combined hearing device and physiologic sensing device comprising one or more microphones, a speaker or receiver, and a sensor facility 134 comprising one or more physiologic sensors. In any of these embodiments, the in-ear component 102 can also include one or more positional sensors.

The on-ear component 104 includes a number of components that can vary depending on the configuration and functionality of the on-ear component 104 and that of the in-ear component 102. Typically, each of the various configurations of the on-ear component 104 includes a number of core components. In the representative embodiment shown in FIG. 5, for example, the core components of the on-ear component 104 include a processor 140 coupled to memory 142, a rechargeable power source 144, charging circuitry 146, and a first interface 156. In addition to the core components shown in FIG. 5, the on-ear component 104 can include additional components, such as any one or any combination of the components shown in the representative embodiment of FIG. 6. For example, the on-ear component 104 can be configured as a hearing device further comprising one or more microphones and a speaker or receiver. In other embodiments, the on-ear component 104 can be configured as a physiologic sensing device further comprising a sensor facility comprising one or more physiologic sensors. In further embodiments, the on-ear component 104 can be configured as a combined hearing device and physiologic sensing device further comprising one or more microphones, a speaker or receiver, and a sensor facility comprising one or more physiologic sensors. In any of these embodiments, the on-ear component 104 can also include one or more positional sensors.

As is further shown in FIG. 5, the second interface 136 of the in-ear component 102 is configured to couple to and decouple from the first interface 156 of the on-ear component 104. Coupling of the second and first interfaces 136, 156 establishes a link 110 between the in-ear component 102 and the on-ear component 104. The link 110 can be a wired link 110a, a wireless link 110b, or a combination of a wired link 110a and a wireless link 110b. The link 110 can be a power link or a combined power and data/signal link. The link 110 can be configured to facilitate the communication of any combination of power, data, and control signals between the in-ear and on-ear components 102, 104 for implementing various processes (e.g., see FIGS. 2-4).

The wired link 110a can comprise an electrical conductor arrangement configured to electrically connect the second and first interfaces 136, 156. For example, the second interface 136 can comprise an elongated flexible connector configured to electrically and mechanically couple to and decouple from the first interface 156 (e.g., via manual force or magnetic attraction (e.g., automatic coupling)). Alternatively, the first interface 156 can comprise an elongated flexible connector configured to electrically and mechanically couple to and decouple from the second interface 136 (e.g., via manual force). In some implementations, both the second interface 136 and the first interface 156 can comprise an elongated, flexible electrical connector. The wireless link 110b can be an inductive link and/or a radiofrequency link established between the second and first interfaces 136, 156. For example, the first interface 156 of the on-ear component 104 can comprise a wireless powering arrangement (e.g., wireless power transmitter) configured to wirelessly couple power to the wireless power receiver 138 of the in-ear component 102.

Figure 6:
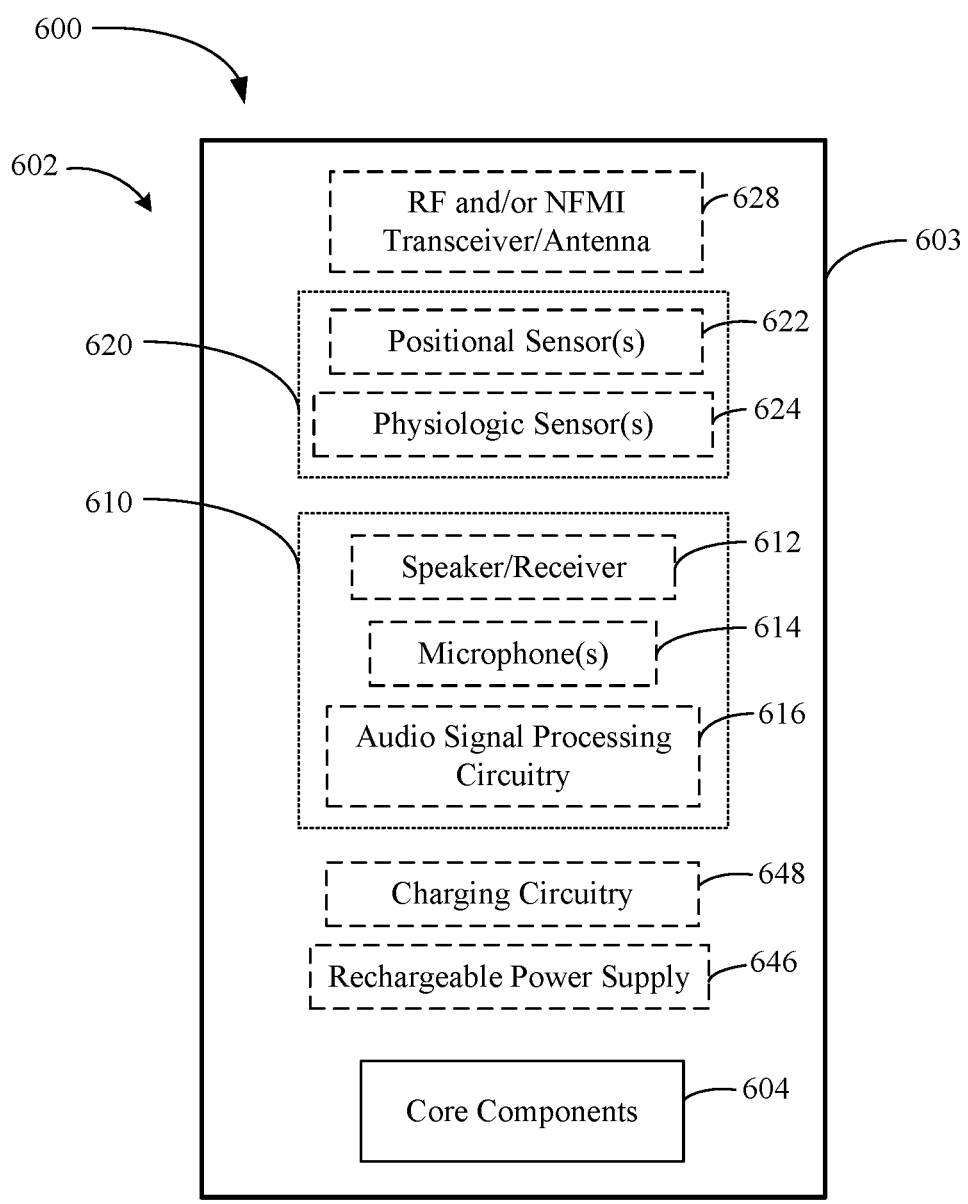
FIG. 6 is a block diagram of an ear-worn electronic device in accordance with any of the embodiments disclosed herein.

According to some embodiments, the in-ear component 102 includes a rechargeable power source coupled to charging circuitry of the power management circuitry 137 (see FIG. 6). As was previously discussed, the rechargeable power source of the in-ear component 102 can be configured to serve as a backup power source in response to failed, interrupted or insufficient reception of power received by the wireless power receiver 138. In such embodiments, the backup power source can be charged using power received by the wireless power receiver 138 when the system 101 is in a decoupled configuration. When the system 101 is in a coupled configuration, the power link 110 can facilitate charging of the rechargeable power source of the in-ear component 102 using the rechargeable power source 144 of the on-ear component 104.

The wireless powering arrangement 125 shown in FIG. 5 includes a power source 160 coupled to a transmitter 162. The transmitter 162 is coupled to, or incorporates, an antenna arrangement 164. The antenna arrangement 164 can include one or more antennas 166, an antenna array 168, or a phased array antenna arrangement 168a. The power source 160 can be configured to receive power from a conventional wall socket and/or include a rechargeable power source (e.g., a lithium-ion battery). The wireless powering arrangement 125 can be a portable arrangement or a positionally fixed arrangement mounted to or on a stationary support structure (e.g., a wall or bed headboard). For example, the wireless powering arrangement 125 can comprise a head-worn device configured to support at least the power transmitter 162 and optionally the power source 160. The head-worn device can comprise a headband or a sleep mask configured to cover the wearer's eyes. The head-worn device can comprise a mask of an apparatus configured to deliver a sleep disordered breathing therapy (e.g., a CPAP mask).

The wireless powering arrangement 125 can be implemented using a number of different technologies for transmitting energy in the form of electromagnetic fields. In general terms, the power transmitter 162 converts power received from the power source 160 and converts this power to an electromagnetic field (e.g., time-varying electromagnetic field). The wireless power receiver 138 of the in-ear component 102 is configured to convert the electromagnetic field to DC and/or AC electric current which is used by electrical and electronic components of the in-ear component 102. The antenna arrangement 164 of the wireless powering arrangement 125 and the wireless power receiver 138 of the in-ear component 102 can have varying configurations depending on the wireless power transfer technology implemented by the monitoring system 100. As such, the antenna arrangement 164 and the wireless power receiver 138 can be implemented to include one or more coils of wire which generate a magnetic field, a metal plate which generate an electric field, or an antenna which radiates electromagnetic waves, for example.

In some configurations, the wireless powering arrangement 125 is configured as a near-field wireless powering arrangement. For example, a near-field wireless powering arrangement 125 can be implemented using a variety of non-radiative technologies for effecting wireless power transfer (WPT) from the transmitter 162/antenna arrangement 164 to the wireless power receiver 138 of the in-ear component 102. According to some configurations, near-field wireless power transfer implemented by the wireless powering arrangement 125 involves the transfer of power over relatively short distances by way of magnetic fields using inductive coupling between coils of wire disposed in the antenna arrangement 164 and the wireless power receiver 138. According to other configurations, near-field wireless power transfer implemented by the wireless powering arrangement 125 involves capacitive coupling between metal electrodes disposed in the antenna arrangement 164 and the wireless power receiver 138.

In other configurations, the wireless powering arrangement 125 is configured as a far-field wireless power arrangement. For example, a far-field wireless powering arrangement 125 can be implemented using a variety of radiative technologies for effecting wireless power transfer from the transmitter 162/antenna arrangement 164 to the wireless power receiver 138 of the in-ear component 102. According to some configurations, far-field wireless power transfer implemented by the wireless powering arrangement 125 involves power beaming, by which power is transferred by beams of electromagnetic radiation emanating from the transmitter 162/antenna arrangement 164 and directed to the wireless power receiver 138 of the in-ear component 102.

The technologies used to implement the wireless powering arrangement 125 can include various short, mid-, and long range technologies. The short range technologies can include inductive coupling (Hz-MHz) implemented using wire coil antennas, capacitive coupling (kHz-MHz) implemented using metal plate electrodes, and magnetodynamic coupling (Hz) implemented using rotating magnets. The mid-range technologies can include resonant inductive coupling (kHz-GHz) implemented using tuned wire coils or lumped element resonators. The long range technologies can include microwave (GHz) or light wave (≥THz) technologies. It is understood that the wireless powering arrangement 125 should be implemented to safely transfer power to the in-ear component 102.

According to some implementations, the antenna arrangement 164 of the wireless power receiver 138 can be configured to provide near-field or far-field beamforming (e.g., beam steering). For example, the antenna arrangement 164 can be configured as a phased array antenna arrangement 168a comprising a power divider 170 coupled to each of a number of antennas 166 via a phase shifter 172 and an amplifier 174. Power radiated by the antenna arrangement 164 can be steered by changing the phases of the electrical signals provided to the individual antennas 166 by a phase control 176. Power radiated by the antenna arrangement 164 can be steered to provide enhanced or optimal transfer of power from the wireless powering arrangement 125 to the wireless power receiver 138 of the in-ear component 102.

For example, the phased array antenna arrangement 168a can be configured to focus radio frequency waves on the wireless power receiver 138 of the in-ear component 102. In some embodiments, the wireless powering arrangement 125 and the in-ear component 102 are configured to communicate with one another to enhance (e.g., optimize) the transfer of power wirelessly from the wireless powering arrangement 125 to the in-ear component 102. For example, the in-ear component 102 can include a first wireless transmitter or transceiver 121 configured to communicate power transfer information to a wireless receiver or transceiver 163 of the wireless powering arrangement 125. The wireless power arrangement 125 can be configured to steer the array of antennas 166 to enhance reception of the radio frequency waves by the wireless charging receiver 138 in response to the power transfer information received from the in-ear component 102. It is understood that radio frequency waves can comprise electric, magnetic, or electromagnetic waves.

FIG. 6 is a block diagram of an ear-worn electronic device 600 in accordance with any of the embodiments disclosed herein. The device 600 is representative of one or both of the in-ear component 102 and on-ear component 104 shown in FIG. 5. The in-ear component 102 and the on-ear component 104 include a number of core components 604 as previously discussed with reference to FIG. 5. In addition to these core components 604, one or both of the in-ear component 102 and the on-ear component 104 can include one or more additional components, representative examples of which are shown in FIG. 6. It is understood that one or both of the in-ear component 102 and the on-ear component 104 can include any one or any combination of the components shown in FIG. 6 or exclude any one or any combination of these components.

With reference to FIGS. 5 and 6, the ear-worn electronic device 600 shown in FIG. 6 includes a number of components in addition to the core components 604 that can vary depending on the configuration and functionality of the in-ear component 102 and that of the on-ear component 104 shown in FIG. 5. The device 600 can include any one or any combination of a sensor facility 620, an audio processing facility 610, and a communication facility 628. The audio processing facility 610 can include audio signal processing circuitry 616, one or more microphones 614, and/or a speaker or receiver 612. The sensor facility 620 can include one or more physiologic sensors 624 and/or one or more positional sensors 622. The device 600 can also include a rechargeable power supply 646 and charging circuitry 648 configured to charge the rechargeable power supply 646.

According to any of the embodiments disclosed herein, the device 600 implemented as an in-ear component 102 can include the rechargeable power supply 646 and charging circuitry 648, and exclude a wireless power receiver 138. In such embodiments, the in-ear component 102 can be operatively coupled to a power source 144 of an on-ear component 104 for charging the rechargeable power supply 646 of the in-ear component 102, such as during the day. Power can be transferred from the on-ear component 104 to the in-ear component 102 via a wired or wireless connection as previously described (e.g., via a detachable, flexible elongated tube containing electrical conductors and electrical contacts). When the on-ear component 104 is operatively decoupled from the in-ear component 102, such as during wearer sleep, the rechargeable power supply 646 is configured to provide power sufficient to allow the in-ear component 102 to operate in a decoupled/stand-alone mode (e.g., for about 8-10 hours). The rechargeable power supply 646 of the in-ear component 102 can again be charged when the in-ear component 102 is operatively coupled to the on-ear component 104, such as when the wearer awakens the next morning. Additional features and/or functions of in- and/or on-ear components that can be incorporated in devices and methods disclosed herein, including those that include or exclude a wireless power receiver 138, are disclosed in commonly owned, U.S. Application Serial Nos. 62/928,652 filed Oct. 31, 2019 and 62/950,864 filed Dec. 19, 2019, both of which are incorporated herein by reference.

The sensor facility 620 can include one or more physiologic sensors 624, one or more positional sensors 622, or a combination of one or more physiologic sensors 624 and one or more positional sensors 622. Representative physiologic sensors 624 include, but are not limited to, an EKG or ECG sensor, a pulse oximeter (e.g., an $SpO_2$ sensor), a respiration sensor, a temperature sensor, a glucose sensor, an EEG sensor, an EMG sensor, an EOG sensor, a blood pressure sensor, or a galvanic skin response sensor. Representative examples of such sensors are disclosed in US Pat. Pub. Nos. 2018/0014784 (Heeger et al.), 2013/0216434 (Ow-Wing), and 2010/0253505 (Chou), and in U.S. Pat. No. 9,445,768 (Alexander et al.) and U.S. Pat. No. 9,107,586 (Bao), each of which is incorporated herein by reference in its entirety. Representative positional sensors 622 include, but are not limited to, accelerometers, gyroscopes, magnetometers, inertial measurement units (IMUs), GPSs or any combination of these sensors.

The communication facility 628 can include a radiofrequency (RF) transceiver and antenna and/or a near field magnetic induction (NFMI) transceiver and antenna. For example, the communication facility 628 can incorporate an antenna arrangement coupled to a high-frequency radio, such as a 2.4 GHz radio. The radio can conform to an IEEE 802.11 (e.g., WiFi®) or Bluetooth® (e.g., BLE, Bluetooth® 4.2, 5.0, 5.1, 5.2 or later) specification, for example. It is understood that the device 600 can employ other radios, such as a 900 MHz radio.

The electronic circuitry of the device 600 can be implemented to incorporate a controller 120 and/or a processor 140. The controller 120 and/or processor 140 can be representative of any combination of one or more logic devices (e.g., multi-core processor, digital signal processor (DSP), microprocessor, programmable controller, general-purpose processor, special-purpose processor, hardware controller, software controller, a combined hardware and software device), filters (e.g., FIR filter, Kalman filter), memory (FLASH, RAM, ROM etc.), other digital logic circuitry (e.g., ASICs, FPGAs), and software/firmware configured to implement the functionality disclosed herein. The electronic circuitry can include or be coupled to one or more types of memory, including ROM, RAM, SDRAM, NVRAM, EEPROM, and FLASH, for example.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. An ear-worn electronic monitoring system configured to be worn by a wearer and powered wirelessly at least during wearer sleep, the ear-worn electronic monitoring system comprising:
   an on-ear component comprising a housing configured for placement on, in or about the wearer's ear, the on-ear component comprising a power source and a first interface coupled to the power source; and
   an in-ear component comprising a housing configured for deployment at least partially within an ear canal of the wearer, the in-ear component comprising:
      a second interface configured to couple to and decouple from the first interface;
      a controller coupled to a memory;
      one or more physiologic sensors coupled to the controller and memory; and
      power management circuitry coupled to the controller and comprising a wireless power receiver configured to receive power from a wireless powering arrangement, the power management circuitry further configured to receive power from the power source of the on-ear component when the second interface is coupled to the first interface.

2. The system according to claim 1, wherein:
   the on-ear component and the in-ear component are configured for deployment and cooperative operation in a coupled mode during wakefulness of the wearer; and
   the in-ear component is configured for deployment without the on-ear component in a decoupled mode during wearer sleep.

3. The system according to claim 1, wherein the in-ear component is devoid of a battery.

4. The system according to claim 1, wherein the in-ear component comprises a rechargeable battery coupled to the power management circuitry and configured to serve as a backup power source in response to failed, interrupted or insufficient reception of power from the wireless powering arrangement.

5. The system according to claim 1, wherein the second interface is configured for wired coupling to the first interface.

6. The system according to claim 1, wherein one of the first and second interfaces comprises an elongated connector configured to electrically and mechanically couple to and decouple from the other of the first and second interfaces.

7. The system according to claim 1, wherein the second interface is configured to wirelessly couple to the first interface.

8. The system according to claim 1, wherein the first interface comprises a wireless powering arrangement configured to wirelessly couple power to the wireless power receiver of the power management circuitry.

9. The system according to claim 1, further comprising:
   an in-the-ear (ITE) device comprising a battery and the wireless powering arrangement configured to wirelessly couple power to the wireless power receiver of the in-ear component during wearer sleep, wherein:
   the on-ear component is configured to provide power to the in-ear component during wearer wakefulness; and
   the ITE device is configured to wirelessly couple power to the in-ear component during wearer sleep.

10. The system according to claim 1, wherein:
    the in-ear component further comprises any combination of a wireless transmitter or transceiver, a speaker or receiver, a microphone or microphones, audio processing circuitry, and a controller or processor; and
    the on-ear component further comprises any combination of a wireless transmitter or transceiver, a speaker or receiver, a microphone or microphones, audio processing circuitry, a controller or processor, and one or more physiologic sensors.

11. The system according to claim 1, wherein the memory is configured to store one or more physiologic signals or sensed physiologic conditions of the wearer generated or acquired by the one or more physiologic sensors.

12. The system according to claim 11, wherein the in-ear component comprises a wireless transceiver configured to communicate physiologic information stored in the memory to a wireless transceiver of the on-ear component or to an external device or system.

13. The system according to claim 1, wherein the on-ear component comprises a memory configured to store the one or more physiologic signals or sensed physiologic conditions of the wearer received from the memory of the in-ear component.

14. The system according to claim 1, wherein:
    the on-ear component comprises a memory and one or more physiologic sensors;
    the memory of the on-ear component is configured to store one or more physiologic signals or sensed physiologic conditions of the wearer generated or acquired by the one or more physiologic sensors of the on-ear component; and
    the memory of the on-ear component is configured to store the one or more physiologic signals or sensed physiologic conditions of the wearer received from a memory of the in-ear component.

15. The system according to claim 14, wherein the on-ear component comprises a wireless transceiver configured to communicate physiologic information stored in the memory of the on-ear component to an external device or system.

16. A system, comprising:
    a wireless powering arrangement comprising a power transmitter; and
    an ear-worn electronic monitoring system configured to be worn by a wearer and powered wirelessly at least during wearer sleep by the wireless powering arrangement, the ear-worn electronic monitoring system comprising:
    an on-ear component comprising a housing configured for placement on, in or about the wearer's ear, the on-ear component comprising a power source and a first interface coupled to the power source; and
    an in-ear component comprising a housing configured for deployment at least partially within an ear canal of the wearer, the in-ear component comprising:

a second interface configured to couple to and decouple from the first interface;

a controller coupled to a memory;

one or more physiologic sensors coupled to the controller and memory; and power management circuitry coupled to the controller and comprising a wireless power receiver configured to receive power from the wireless powering arrangement, the power management circuitry further configured to receive power from the power source of the on-ear component when the second interface is coupled to the first interface.

17. The system according to claim 16, wherein the wireless powering arrangement is configured as a near-field wireless powering arrangement.

18. The system according to claim 16, wherein the wireless powering arrangement is configured as a far-field wireless powering arrangement.

19. The system according to claim 16, wherein the wireless powering arrangement comprises a head-worn device configured to support the power transmitter.

20. The system according to claim 19, wherein the head-worn device comprises a battery configured to supply power for the wireless powering arrangement.

21. The system according to claim 19, wherein the head-worn device comprises a headband, a sleep mask configured to cover the wearer's eyes, or a mask of an apparatus configured to deliver a sleep disordered breathing therapy.

22. The system according to claim 16, wherein the power transmitter of the wireless powering arrangement incorporates or is coupled to an array of antennas configured to focus radio frequency waves on the wireless power receiver of the in-ear component.

23. The system according to claim 16, wherein:

the in-ear component comprises a first wireless transmitter or transceiver configured to communicate power transfer information to a wireless receiver or transceiver of the wireless powering arrangement; and the wireless powering arrangement is configured to steer the array of antennas to enhance reception of the radio frequency waves by the wireless charging receiver in response to the power transfer information received from the in-ear component.

24. A method of powering an ear-worn electronic monitoring system configured to be worn by a wearer, the method comprising:

powering, during wearer wakefulness, an in-ear component of the monitoring system using a power source of an on-ear component of the monitoring system;

powering, during wearer sleep and with the on-ear component decoupled from the in-ear component, the in-ear component using a wireless power receiver of the in-ear component operatively coupled to a wireless powering arrangement; and operating, during wearer sleep, the in-ear component using power received from the wireless powering arrangement via the wireless power receiver of the in-ear component.

25. The method according to claim 24, wherein powering the in-ear component during wearer wakefulness comprises supplying power from the power source of the on-ear component to power management circuitry of the in-ear component via a wired connection.

26. The method according to claim 24, wherein powering the in-ear component during wearer wakefulness comprises wirelessly supplying power from the power source of the on-ear component to the wireless power receiver in-ear component.

27. The method according to claim 24, comprising:

sensing, during wearer sleep, one or more physiologic parameters or conditions of the wearer using one or more sensors of the in-ear component;

storing, during wearer sleep, physiologic data indicative of the sensed one or more physiologic parameters or conditions of the wearer in a memory of the in-ear component; and communicating, during wearer wakefulness, the physiologic data stored in the memory of the in-ear component to a memory of the on-ear component or an external electronic device.

* * * * *